United States Patent [19]

Ikeda et al.

[11] 4,126,032
[45] Nov. 21, 1977

[54] METHOD AND APPARATUS FOR DETERMINING PHOTO-CHEMICAL REACTION HEAT

[75] Inventors: Mitsuru Ikeda; Teppei Ikeda, both of Asaka; Yoshihiko Teramoto, Tokyo; Masatoshi Yasutake, Tokyo; Yoshimi Nakamine, Tokyo, all of Japan

[73] Assignees: Kabushiki Kaisha Daini Seikosha; Fuji Film Co., Ltd., Japan

[21] Appl. No.: 778,035

[22] Filed: Mar. 16, 1977

[30] Foreign Application Priority Data

Mar. 23, 1976 [JP] Japan .................................. 51-31667
Mar. 23, 1976 [JP] Japan .................................. 51-31668

[51] Int. Cl.$^2$ ......................................... G01K 17/00
[52] U.S. Cl. ................................ 73/15 B; 73/190 R; 23/230 R; 422/51
[58] Field of Search ........... 73/15 B, 190 R, 190 EW; 23/230 R, 253 R

[56] References Cited

U.S. PATENT DOCUMENTS

| | | | |
|---|---|---|---|
| 2,800,793 | 7/1957 | Oliver | 73/190 |
| 3,245,758 | 4/1966 | Benzinger et al. | 73/190 X |
| 3,314,288 | 4/1967 | Sherwin | 73/190 |
| 3,379,061 | 4/1968 | Mercier | 73/190 |
| 3,473,382 | 10/1969 | Tabeling | 73/15 X |
| 3,641,444 | 2/1972 | Watts | 73/190 X |
| 3,858,433 | 1/1975 | Nearhoof | 73/15 |

OTHER PUBLICATIONS

Gunn "Volume Absorbing Calorimeters for High-Power Laser Pulses", in Rev. Sci. Instrum, vol. 45 #7 (7-74) pp. 936-943.

*Primary Examiner*—Herbert Goldstein
*Attorney, Agent, or Firm*—Robert E. Burns; Emmanuel J. Lobato; Bruce L. Adams

[57] ABSTRACT

A system for determining photo-chemical reaction heat evolved from a sample material irradiated with radiant energy comprises a calorimeter having a pair of sample holders connected to heat-leakage type thermo-electric elements which develop electric output signals proportionate to the amount of heat energy conducted therethrough. Both sample holders are initially irradiated with radiant energy before disposing the sample material thereon to heat the sample holders and thereby develop electric output reference signals. The amount of radiant energy being irradiated on at least one of the sample holders is then selectively adjusted to effectively compensate for any difference between the two reference signals. Then the sample material is mounted on at least one of the sample holders and both sample holders are irradiated with the adjusted radiant energy thereby enabling determination of the exothermic or endothermic heat value generated by the sample material due to the photo-chemical reaction heat evolved therefrom in accordance with the difference in the electric output signals developed by said thermo-electric elements.

3 Claims, 4 Drawing Figures

METHOD AND APPARATUS FOR DETERMINING PHOTO-CHEMICAL REACTION HEAT

BACKGROUND OF THE INVENTION

The present invention relates to a method and apparatus for determining photo-chemical reaction heat occurring when sensitive material reacts photo-chemically.

Applying high energy radiant rays such as light, to photo-sensitive material, such as photo-sensitive resin, causes a photo-chemical reaction such as photo-polymerization to be produced. At that time, exothermic or an endothermic reaction is generated. It is significant in determining optimum reaction conditions to determine the reaction heat produced during the photo-chemical reaction and furthermore to thereby determine the reaction velocity.

In the prior art, there has been used a calorimeter for determining the changes in fusing, transition, decomposition or the like which are caused when the temperature of certain material is raised for determining the thermal changes, such as exothermic or endothermic change, generated when different materials are mixed. However, in the prior art, there has not been such apparatus by which the exothermic or endothermic value may be determined when a certain material is added to a different material during the photo-chemical reaction under the above-mentioned fixed temperature.

In the above-mentioned determination, since the reaction velocity in photo-reaction differs or varies according to the temperature of the sample itself, it is required that the temperature of the surrounding atmosphere be maintained at a fixed value and that the temperature of the sample be maintained at a fixed one. However, even when the surrounding temperature is maintained constant, the temperature of the sample itself changes due to the reaction heat generated when the sample itself is reacted. Therefore, it becomes difficult to carry out the determination of the photo-chemical reaction heat with high accuracy.

SUMMARY OF THE INVENTION

It is an object of the present invention to provide a method and an appratus for determining exothermic or endothermic heat valves generated owing to the decomposition, polymerization or the like occurring when the stimulation such as light is exerted on the sensitive material.

It is another object of the present invention to provide a method and an apparatus for determining precisely, without thermal noise or obstruction, the photo-chemical reaction heat and the reaction velocity caused when radiant energy is applied to the sensitive material.

It is another object of the present invention to provide a method and an apparatus for precisely determining the photo-chemical reaction heat in which the determination of the photo-chemical reaction heat may be carried out without receiving influences such as the differences in thermal capacity or heat conductivity of plates between a reference and sample portions of the determination apparatus.

These and other objects may be achieved in such a manner that the sample plate is located in a thermostat through a heat-leakage type temperature detector, the reaction heat is made to be fast leaked into the thermostat whereby the large change in the sample temperature may be prevented, two sample plates are disposed at positions thermally equal to each other and the radiant ray is simultaneously applied to both the sample plates, the sample being mounted on only one sample plate so as to determine the exothermic or endothermic value in accordance with the difference in temperature between both the sample plates.

DETAILED DESCRIPTION OF THE PREFERRED EMBODIMENTS

Figure 1:
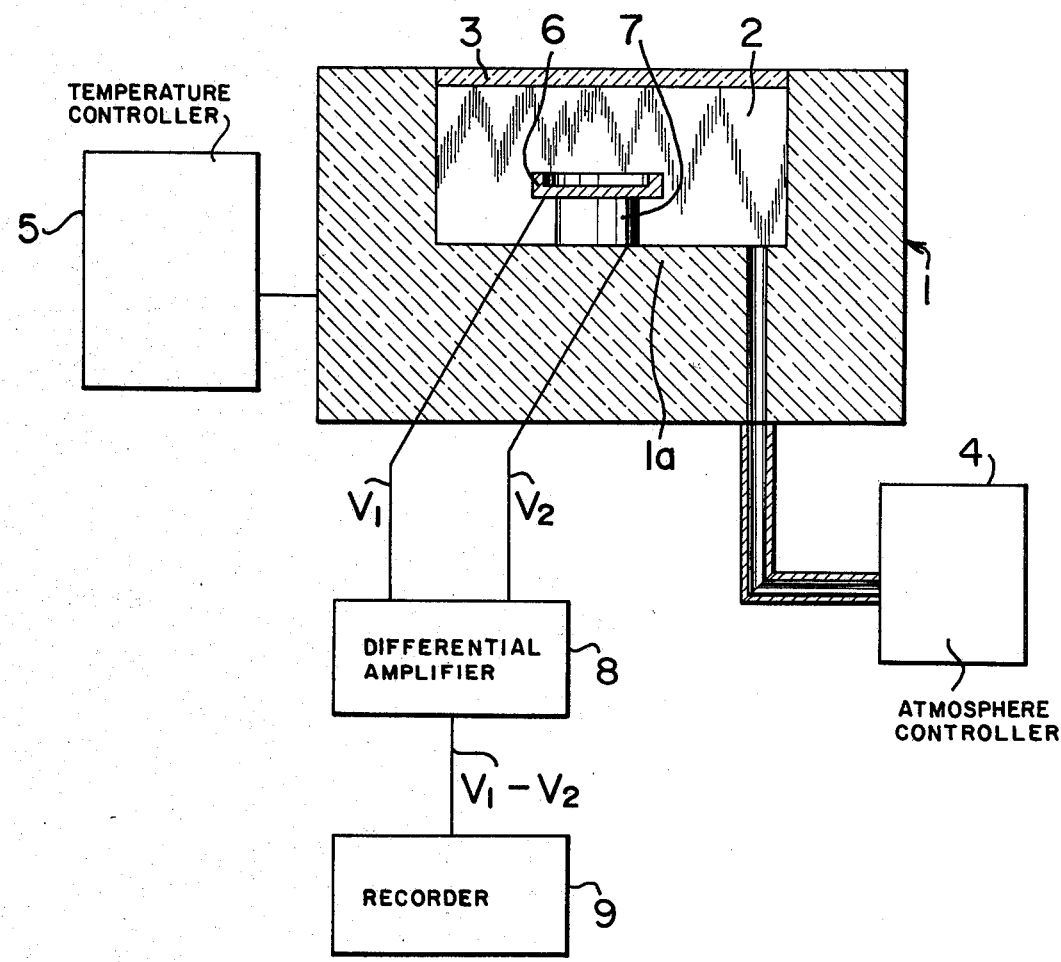
FIG. 1 is a schematic explanatory view of a photo-chemical reaction heat determination apparatus of the present invention.

The preferred embodiments of the invention will be explained hereinbelow in conjunction with the accompanying drawings.

In the drawings, 1 shows a thermostat of a calorimeter, 2 is a constant temperature chamber located in a center position of the thermostat 1. The upper portion of this constant temperature chamber 2 is closed by a glass plate 3.

4 designates an atmosphere controller which makes the interior of said constant temperature chamber 2 vacuous and to be filled with gas, such as $N_2$ gas, that does not react with the sample in order to control the atmosphere during the photo-chemical reaction. 5 is a temperature controller which keeps the temperature of the entire body of said thermostat 1 at a predetermined value. For instance, in the wall of the thermostat 1, is disposed circulation pipe (not shown) into which a temperature controlled fluid is circulated, whereby the temperature of the thermostat 1 may be kept at a fixed temperature.

6 is a holder for mounting the sample plate thereon. Said sample plate is placed in said constant temperature chamber 2. This holder 6 is thermally closely attached on a heat sink $1a$ of the thermostat 1 through a heat-leakage type thermo-electric element 7 which is comparatively sufficient in heat conductivity and large in sectional area (for instance, a semi-conductor temperature detector such as a thermo-module). This thermo-electric element 7 detects a minimum difference in temperature between a portion closely contacting a lower surface of said holder 6 and a portion closely contacting an upper portion of the heat sink $1a$, that is to say, the quantity of heat per unit time leaking out of and conducting through the thermo-electric element 7 and generates an output voltage corresponding thereto.

8 is a differential amplifier the which amplifies potential difference between both ends of said thermoelectric element 7 ($V_1-V_2$).

9 is a recorder which records the output from the differential amplifier 8.

The operation of the apparatus according to the present invention will be described hereinafter in detail.

When radiant energy such as light is applied through the glass plate 3 to the sample (after actuating said temperature controller 5 with the thermostat 1 maintained at a predetermined temperature and with the sample disposed in a sample plate on the holder 6,) the photo-chemical reaction occurs in a sample accompanied by the exothermic or endothermic reaction. A difference in temperature (about 0.01k) is thus developed between the holder 6 and the heat sink 1a and the quantity of heat produced by this temperature differential is conducted through the thermo-electric element 7. Due to this thermal conduction there occurs a potential difference corresponding thereto at both the ends of the thermo-electric element 7. This potential difference is amplified by means of the differential amplifier 8 and the obtained results are recorded as a function of time by the recorder 9. Thus, the progress of the photo-chemical reaction may be read and the integrated value of the above recorded value is equivalent to the total exothermic or endothermic heat value of the sample during the photo-chemical reaction.

Therefore, in accordance with the method of the present invention, heat generated in the sample is constantly to be transferred to a heat sink 1a through the thermo-electric element 7. Since the heat sink 1a has a satisfactorily large heat capacity, the temperature thereof scarcely changes. Also, since the heat conductivity of the thermo-electric element 7 is sufficiently good, the temperature of the sample itself scarcely changes and therefore the reaction progresses at the atmosphere temperature which is almost equal to the predetermined temperature.

Instead of the sample, material having the same heat capacity as the sample may be mounted on the sample plate. (Or nothing may be mounted on the sample plate). Then radiant energy is applied to the sample mounted on the sample plate, the thermal change of the holder at that time is examined in advance in order to compensate the actually determined value, whereby a true reaction heat in which the quantity of heat of the radiant ray absorbed in the holder or the sample plate is eliminated may be determined.

Figure 2:
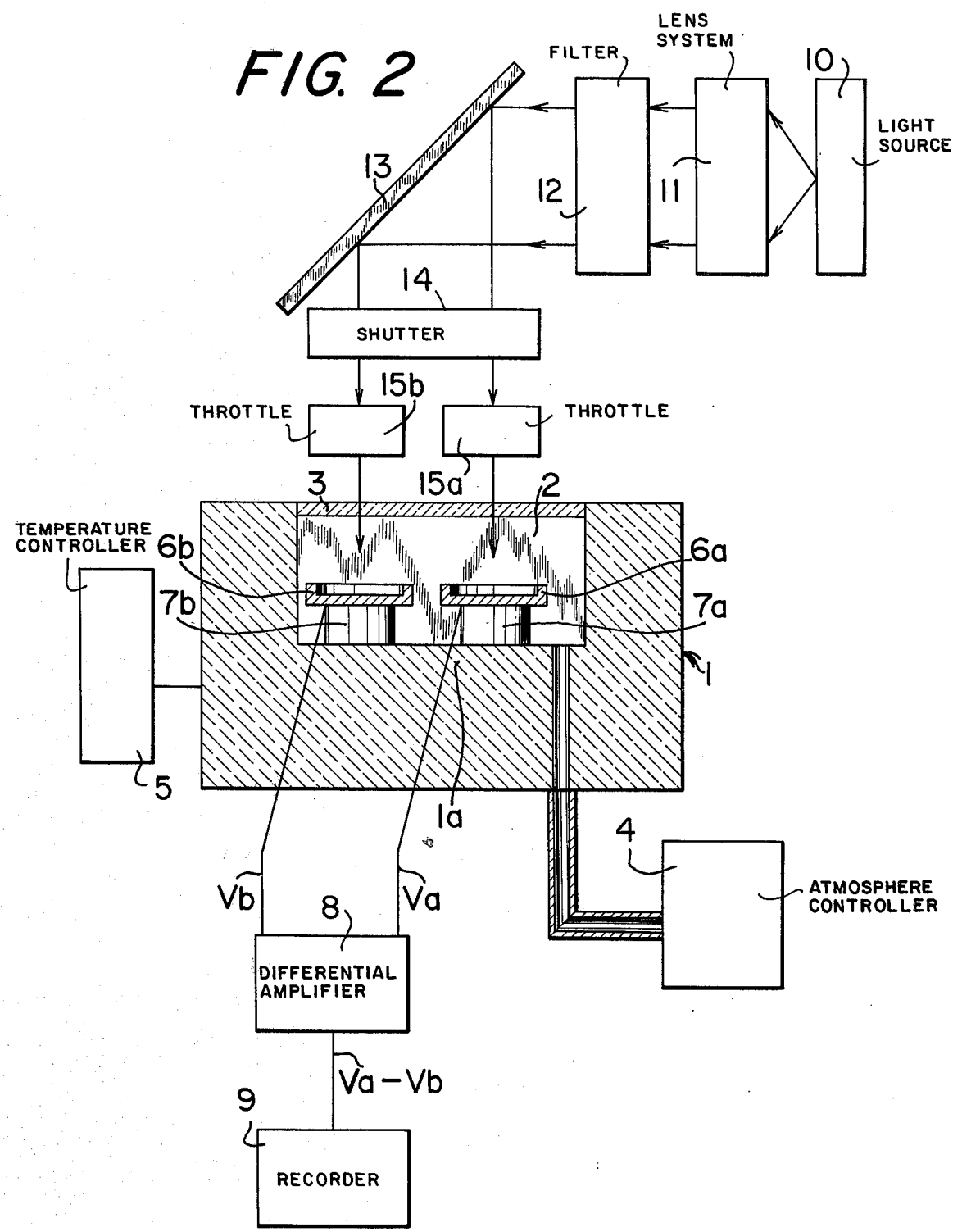
FIG. 2 is a schematic explanatory view showing an embodiment of the present invention.

FIG. 2 is another embodiment of the present invention which shows a twin type calorimeter adapted to compensate for the influences of thermal change due to the radiant energy during the determination of the reaction heat. Holders 6a and 6b are arranged through thermo-electric elements 7a and 7b at thermally equal positions in the constant temperature chamber 2. On one holder 6a, the sample plate containing the sample is mounted and on the other holder 6b, the sample plate on which a comparative material which does not exhibit photo-chemical reaction is mounted. The potential difference (Va-Vb) between portions closely contacting with said holders 6a and 6b of the respective thermo-electric elements 7a and 7b is amplified suitably by means of the differential amplifier 8. The difference in temperature between the holder 6a of the sample side and the holder 6b of the reference side is recorded on the recorder 9.

In this case, 10 is a light source for generating the radiant rays such as xenon lamp, super high mercury lamp, metal halide lamp, laser etc. Said light source may be selected suitably according to the reacting material. 11 is a lens system which collimates the light applied from the light source 10 into parallel light rays. 12 is a filter which passes light rays of a desired wave length or wave lengths in a proper range among these parallel light rays. A light source system comprises the above-mentioned light source 10, the lens system 11 and the filter 12. This light source system may be replaced by a laser apparatus.

13 is a reflection mirror for reflecting parallel rays emitted from the light source system downwards. 14 is a shutter for controlling the applied time of the reflected light rays. 15a and 15b are variable throttles which are arranged at the underside of the shutter 14 and in parallel with each other and adjust the amount of said reflected light rays. The sample plates to which the sample is not painted are initially mounted on the holders 6a and 6b. The light rays emitted from the light source system are applied to the sample plates. The temperature of the sample plates rises owing to the energy of the light rays which is detected by the thermo-electric elements 7a and 7b. The variable throttles 14a and 14b are adjusted so as to make the difference in temperature between both the sample plates zero, thereby the rise of temperature of both the sample plates can be equalized.

Figure 3:
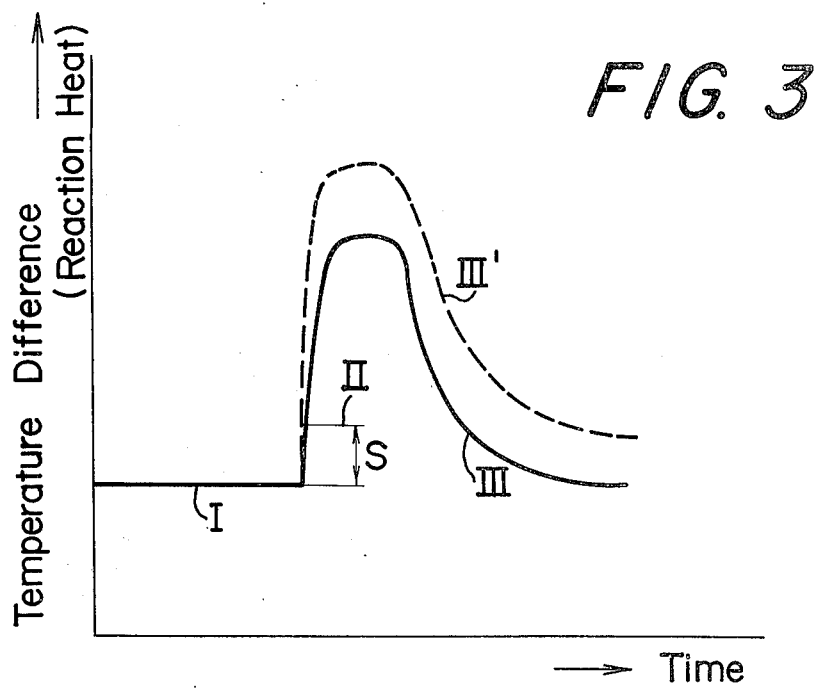
FIG. 3 is a graph showing a photo-chemical reaction curve recorded on a recorder.

Furthermore, in order to determine the reaction heat of the sensitive material accurately, at first, the material which has the same heat capacity as the sample and does not exhibit photo-chemical reaction is mounted on the holders 6a and 6b respectively. The temperature controller 5 is actuated so as to maintain the temperature of the thermostat 1 at a predetermined value. The shutter 14 is opened thereafter in order to apply the light from the light source system to the holders 6a and 6b. Then, the energy of the light rays is absorbed by the holders and the temperature of the holders rises. At this time, due to the difference in heat capacity or the like of the holders or the thermo-electric elements, there occurs the difference in temperature or the potential difference between the thermo-electric elements 7a and 7b. Accordingly, a base line shifts in the recorder 9. Variable throttles 15a and 15b are adjusted so as to return the changed line to base line I by compensating the changed line by the amount of this shift (shown by s in FIG. 3). Consequently, the difference in levels between the electric signals output from both the thermo-electric elements are compensated.

After the above-described compensation is completed, the sample is mounted on one holder 6a and the comparative material which has the same heat capacity as the sample and does not react photo-chemically is mounted on the other holder 6b. The shutter 14 is opened again and the light rays are applied to both the sample side and the reference side.

Then, due to these light rays, the sample produces the photo-chemical reaction and exhibits the exothermic or endothermic phenomena. The temperature of the sample side or the holder is changed (about 0.01k) and the heat is transferred to the heat sink 1a through the thermo-electric element 7a. In this manner, an output voltage is generated in the thermo-electric elements 7a and 7b. The difference in temperature or the difference in level (a-b) of the electric signals between the sample side and the reference side are properly amplified and recorded as function of time in the recorder. At this time, since the shift of the base line caused by the heat capacity of both the holders and the heat conductivity of the thermo-electric elements has already been compensated, a true reaction curve III is recorded in said recorder 9.

Therefore, from this reaction curve III, the precise progress of the photo-chemical reaction may be read and also the integrated value of this recorded value is adapted to be equivalent to total the exothermic value (endothermic value) of the sample during the photo-chemical reaction.

Figure 4:
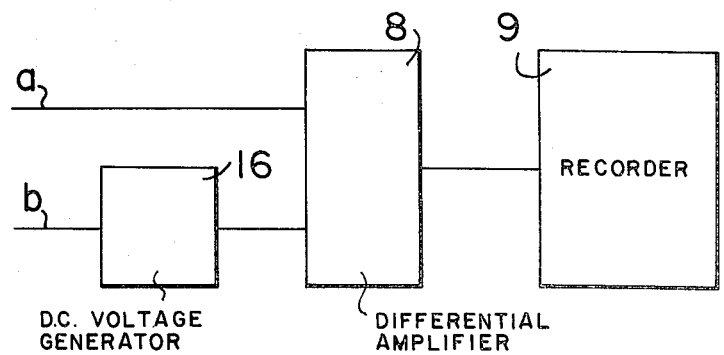
FIG. 4 is a block diagram showing another embodiment of the present invention.

The shift of the line may be compensated by any other method than by adjusting the quantity of the applied radiant energy (quantity of light) by the use of the variable throttle as mentioned in the above embodiment. In short, as shown in FIG. 4, for instance, output signal b fed from one thermo-electric element 6b is input to the differential amplifier 8 after a suitable quantity of DC voltage is adjusted through a DC voltage generator 16, whereby the shift of the base line may be compensated similarly to the above-said embodiment. In this case, the same comparative materials are mounted beforehand on both the holders. The outputs from the thermo-electric elements 7a and 7b when the light rays are applied to the comparative materials is detected. Based upon this output, the value of DC voltage adjusted by the DC voltage generator 16 is determined.

In case of cancelling the difference in level of the electric signals fed from the thermo-electric elements or the shift of the base line, the comparative material to be mounted on the holder may be omitted so as to apply the radiant rays directly to the holder.

Also, the comparative material may be omitted during the determination of the reaction heat of the sample.

In the above-mentioned embodiment, material closely contacting the thermo-electric element in the lower surface of the holder is used for mounting the sample thereon. The bottom portion of the holder may be made as part of the thermo-electric element itself in order to heighten heat conductivity between the holder and the thermo-electric element.

As afore-mentioned, the calorimeter is made as a twin-type and the reaction heat of the sample is adapted to be determined in comparison with the reference side. Therefore, even if the temperature of the thermostat is subjected to thermal noise or obstructions, the exothermic heat or endothermic value may be determined with high accuracy without being influenced by said thermal noise or obstructions.

Moreover, it is apparent that the calorimeter of the present invention is constructed in such a manner that after the radiant rays are applied to a pair of holders and the difference in level of the electric signals output out of the thermo-electric elements are compensated, the sample is mounted on at least one of the holders and the radiant rays are applied simultaneously to the holder on which said sample is mounted and the holder on which said sample is not mounted so as to determine the exothermic or endothermic heat value produced due to the photo-chemical reaction of the sample, in accordance with the difference in output between both the thermo-electric elements. Accordingly, even if there are differences in the heat capacity between two holders, the heat capacity or the heat conductivity between the respective thermo-electric elements or the heat capacity or the like between the sample and the comparative material, a true reaction heat, reaction velocity, reaction continuing time or the like may be determined with excellent and high accuracy without accepting the above thermal conditions.

What is claimed is:

1. A method for determining photo-chemical reaction heat evolved from a sample material irradiated with radiant energy within a calorimeter comprising the steps of: providing a calorimeter having a pair of sample holders connected to heat-leakage type thermo-electric elements which develop electric output signals proportionate to the amount of heat energy conducted therethrough; irradiating both sample holders with radiant energy before disposing the sample material thereon to heat said holders and develop electric output reference signals therefrom; adjusting the amount of radiant energy being irradiated on at least one of said sample holders to effectively compensate for any difference between the two reference signals; and then mounting a sample material on at least one of said sample holders and irradiating both sample holders with the adjusted radiant energy and determining the exothermic or endothermic heat value generated by the sample material due to the photo-chemical reaction heat evolved therefrom in accordance with the difference in the electric output signals developed by said thermo-electric elements.

2. A method according to claim 1; wherein said adjusting step comprises selectively adjusting the amount of radiant energy being irradiated on both sample holders until the two reference signals are equal.

3. An apparatus for determining photo-chemical reaction heat evolved from a sample material irradiated with radiant energy comprising: a calorimeter having an interior chamber the temperature of which is maintained at a predetermined value; a pair of sample holders for holding thereon sample material mounted within said chamber; a pair of heat-leakage type thermo-electric elements connected to respective ones of said sample holders and operable to develop electric output signals proportionate to the amount of heat energy conducted therethrough; means for applying radiant energy to the sample material held on said sample holders; means for determining the quantity of heat conducted by said thermo-electric elements in accordance with the electric signals developed by said thermo-electric elements; and means for compensating for any difference in level between the electric output signals from said thermo-electric elements so as to shift the base line of the sample material to coincide with that of a predetermined reference time-temperature difference characteristic, said means for compensating comprising a variable throttle for selectively adjusting the amount of radiant energy.

* * * * *